(12) United States Patent
Jass et al.

(10) Patent No.: US 7,294,736 B2
(45) Date of Patent: Nov. 13, 2007

(54) PROCESS FOR PREPARATION OF PROBUCOL DERIVATIVES

(75) Inventors: Paul Alan Jass, Charles City, IA (US); Jason Scott Douglas, Charles City, IA (US)

(73) Assignee: Cambrex Charles City, Inc., Charles City, IA (US)

( * ) Notice: Subject to any disclaimer, the term of this patent is extended or adjusted under 35 U.S.C. 154(b) by 450 days.

(21) Appl. No.: 10/821,426

(22) Filed: Apr. 9, 2004

(65) Prior Publication Data

US 2005/0228192 A1 Oct. 13, 2005

(51) Int. Cl.
*C07C 69/017* (2006.01)
(52) U.S. Cl. ........................ 560/142; 560/145
(58) Field of Classification Search ............ None
See application file for complete search history.

(56) References Cited

U.S. PATENT DOCUMENTS

| | | | |
|---|---|---|---|
| 3,485,843 A * | 12/1969 | Wang ................ 544/403 |
| 5,262,439 A | 11/1993 | Parthasaratay et al. |
| 5,380,747 A | 1/1995 | Medford et al. |
| 5,750,351 A | 5/1998 | Medford et al. |
| 5,773,201 A | 6/1998 | Fujimura et al. |
| 5,773,209 A | 6/1998 | Medford et al. |
| 5,807,884 A | 9/1998 | Medford et al. |
| 5,811,449 A | 9/1998 | Medford et al. |
| 5,846,959 A | 12/1998 | Medford et al. |
| 5,877,203 A | 3/1999 | Medford et al. |
| 6,323,359 B1 | 11/2001 | Jass |
| 6,548,699 B1 | 4/2003 | Somers |

* cited by examiner

*Primary Examiner*—Thurman K. Page
*Assistant Examiner*—Yevgeny Valenrod
(74) *Attorney, Agent, or Firm*—Richard J. Hammond

(57) ABSTRACT

A method is described for the preparation of polymorphic forms of water-soluble derivatives of probucol compounds having the following formula Formula 2

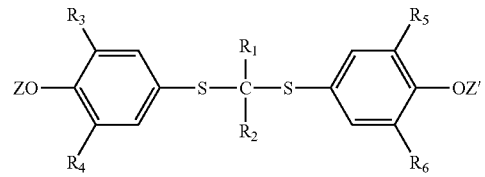

where $R_1$, $R_2$, $R_3$, $R_4$, $R_5$, $R_6$, Z and Z' are defined herein.

12 Claims, No Drawings

PROCESS FOR PREPARATION OF PROBUCOL DERIVATIVES

FIELD OF INVENTION

The present invention relates to 4,4'-(isopropylidenedithio) bis[2,6-di-tert-butylphenol], known and referred to herein by its generic name "probucol", and to derivatives of probucol. More particularly, this invention relates to an improved process for the preparation of probucol derivatives

BACKGROUND OF THE INVENTION

Probucol is a well-known antioxidant that is related to antioxidant compounds such as 2-(3)-tertiary butyl-4-hydroxyanisole, 2,6-di-tertiary butyl-4-methylphenol and the like. These compounds are used in food and food products to prevent oxidative deterioration.

Probucol is represented by the following structural formula

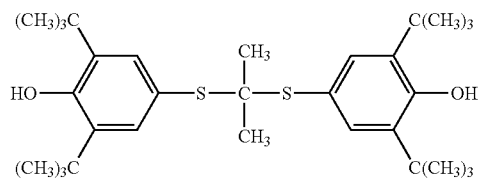

The preparation of this compound is a multistep process, typically starting by reacting a solution of the appropriately-substituted 4-mercaptophenol with acetone, in the presence of a catalytic amount of a strong acid. Probucol precipitates from the reaction mixture and is readily separated and purified. The reaction is described in detail in U.S. Pat. No. 3,862,332 (Barhhart et al).

Similarly, probucol and certain of its derivatives are also described in U.S. Pat. No. 3,485,843 (Wang), U.S. Pat. No. 3,576,833 (Neuworth) and U.S. Pat. No. 4,985,465 (Handler).

Probucol and its derivatives possess pharmaceutical properties that include antiatherogenesis, lipid lowering and the like. But probucol and numerous of its derivatives are poorly soluble in body fluids.

In order to avoid the low water solubility problems associated with probucol utilization in the body, more water-soluble derivatives have been prepared. Thus, U.S. Pat. No. 5,262,439 (Parthasarathy), incorporated herein in its entirety by reference, discloses a class of water-soluble probucol derivatives having one or more ester groups replacing the phenolic hydroxyl group of the probucol molecule. Some of the compounds disclosed in this reference have polar or charged functionalities attached to the ester group, e.g., the groups carboxylic acid, amide, amino, and aldehyde. The method disclosed for preparing these water-soluble probucol compounds involves the reaction of probucol with the carboxylic acid anhydride compound bearing the desired polar or charged functionality in the presence of a catalyst.

Similarly, U.S. Pat. Nos. 6,323,359 and 6,548,699 also disclose water soluble derivatives of probucol. The compounds set forth in the former patent are produced by a process involving the reaction of a probucol dianion with carboxylic acid anhydrides. The compounds disclosed in U.S. Pat. No. 6,548,699 are synthesized by reaction of probucol with, inter alia, halo-substituted aliphatic esters.

The prior art processes are disadvantageous, since they are not effective in producing the desired alkylated derivatives of probucol in any appreciable yields.

Accordingly, it is desirable to have available a process to efficiently prepare probucol derivatives in high yields.

SUMMARY OF THE INVENTION

The process of the present invention is an improvement in a process whereby probucol is reacted with an alkali metal or ammonium-containing compound to produce, as a mixture, the mono- and dialkali metal salts of probucol, e.g, the mono- or dialkali metal salt of 4,4'-(isopropylidenedithio) bis[2,6-di-tert- butylphenol] or its derivatives. This anionic intermediate mixture is then reacted with a carboxylic acid anhydride such as succinic acid anhydride, glutaric acid anhydride, adipic acid anhydride, suberic acid anhydride, sebacic acid anhydride, azelaic acid anhydride, phthalic acid anhydride or maleic acid anhydride to form a reaction mixture of dicarboxylic acid-substituted probucol compounds. These water soluble probucol compounds are then separated from said reaction mixture.

The improved prior art process comprises carrying out the first step of the reaction that produces the mono or dialkali metal salts by using, as a solvent, a compound having the formula R—C(O)—R', where R and R' are the same or different and are $C_1$ to $C_6$ alkyl, $C_2$ to $C_6$ alkenyl, $C_6$ to $C_{12}$ aryl, $C_6$ to $C_{12}$ aryl substituted with at least one $C_1$ to $C_6$ alkyl, $C_5$ to $C_{12}$ heteroaryl or $C_5$ to $C_{12}$ heteroaryl substituted with at least one $C_1$ to $C_6$ alkyl.

DESCRIPTION OF THE PREFERRED EMBODIMENTS

The present invention provides a process for preparing certain water soluble probucol derivatives.

As used herein, the term "$C_1$ to $C_8$ alkyl" is intended to mean and include the groups that are $C_1$ to $C_8$ linear or branched alkyl which include the moieties methyl, ethyl, n-propyl, isopropyl, butyl, sec-butyl, tert-butyl, n-pentyl, 2-methylpentyl, n-heptyl, n-octyl and the like.

The term "$C_6$ to $C_{12}$ aryl" is intended to mean and include the aromatic radicals having 6 to 12 carbon atoms in the aromatic ring system that may be substituted or unsubstituted one or more times by alkyl, nitro or halo which includes phenyl, naphthyl, phenanthryl, anthracenyl, thienyl, pyrazolyl and the like.

The term "$C_3$ to $C_6$ alkenyl" is intended to mean and include the groups that are $C_3$ to $C_6$ linear or branched alkenyl which include the moieties 1-propenyl, 1-butenyl, 2-butenyl, 1-pentenyl, 2-pentenyl and the like.

The term "alkali metal" is intended to mean those metals in Group I and Ia of the Periodic Table of the Elements such as lithium, potassium, sodium and the like.

The water-soluble derivatives of the probucol compounds herein are obtained by reaction of a solution of one or both of the hydroxyl groups of probucol or the probucol derivative with a compound that forms an alkali metal or ammoniun salt of probucol, i.e., the alkali metal or ammonium substitutes for hydrogen at one or both of probucol's hydroxyl groups. The compounds that form these salts are strongly basic reactants. They are illustrated by the alkali metal hydrides, alkali metal hydroxides, alkali metal alkoxides, alkyl ammonium alkoxides or alkyl ammonium hydroxides. Mixtures of these compounds are also useful in producing the desired probucol salts. Potassium is the most preferred alkali metal of these strongly basic reactants used in this step. The process is described in U.S. Pat. No. 6,323,359 and is incorporated herein by reference.

It has been discovered that by using a ketone solvent in this salt-forming reaction, that yields of product probucol compounds are enhanced. The ketone solvent used to carry out this salt-forming reaction has the formula R—C(O)—R', where R and R' are the same or different and are $C_1$ to $C_6$ alkyl, $C_3$ to $C_6$ alkenyl, $C_6$ to $C_{12}$ aryl, $C_6$ to $C_{12}$ aryl substituted with at least one $C_1$ to $C_6$ alkyl, $C_5$ to $C_{12}$ heteroaryl or $C_5$ to $C_{12}$ heteroaryl substituted with at least one $C_1$ to $C_6$ alkyl. Mixtures of these ketone solvents may also be used.

It is preferred that R and R' are the same or different and are $C_1$ to $C_6$ alkyl, most preferably the groups methyl or ethyl. Particularly preferred for the solvent in this reaction is acetone.

The concentration of probucol or its derivatives in the above salt-forming reaction is dramatically higher than that disclosed in similar prior art reactions. Thus, in carrying out the salt-forming reaction, the ratio to solvent to probucol derivative by weight is from about 2:1 to about 1:5, preferably about 1:1 to about 3:10, most preferably 3:5.

A further advantage of the reaction of probucol of the probucol derivative with the alkali metal or ammonium compounds lies in the discovery that the reaction temperature is critical to effecting enhanced salt-forming conversions. Thus, the salt-forming reaction is carried out at temperatures from about 15° to about 75° C., preferably from about 30° to about 60° C., most preferably from about 35° to about 45° C.

Thus, this first reaction in the process (reaction step 1) of the present invention described above, produces a mixture of mono- and dianions of the following Formula 1 (where each A may a proton, an alkali metal cation or an ammonium cation)

Formula 1

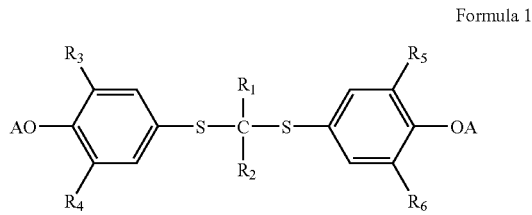

where $R_1$ and $R_2$ are the same or different and are alkyl, alkenyl or aryl having from 1 to 8 carbon atoms and $R_3$, $R_4$, $R_5$ and $R_6$ are the same or different and are alkyl having from 1 to 4 carbon atoms.

Preferably, $R_1$ and $R_2$ are the same and are alkyl having from 1 to 6 carbon atoms, most preferably methyl.

Preferably $R_3$, $R_4$, $R_5$ and $R_6$ are the same and are alkyl having from 1 to 4 carbon atoms, most preferably tert-butyl The mixture of mono- and dialkali metal or ammonium salt of the probucol derivative readily forms in as little as 30 minutes or up to about six hours after such admixing, typically at about 40° C. The diphenolate salt may be removed from the reaction solution as a solid (by precipitation and filtration, etc.) and subsequently used in step 2 of the process, or the reaction solution resulting from step 1 of the reaction can be used "as is" for the second step, i.e., without separating the mixture of mono- and dianions. In either case, the salt produced in the first step is treated with the acid anhydride which reacts with at least one of the alkali metal or ammonium probucol phenolates. However, it should be noted that because there are two reactive sites available in the mono- and dianionic mixture, either one or both of these sites can be substituted by the incoming acid anhydride moiety.

The subsequent reaction of the compounds of Formula 1 with an acid anhydride such as succinic acid anhydride, glutaric acid anhydride, adipic acid anhydride, suberic acid anhydride, sebacic acid anhydride, azelaic acid anhydride, phthalic acid anhydride or maleic acid anhydride produces the compounds of the Formula 2 below Formula 2

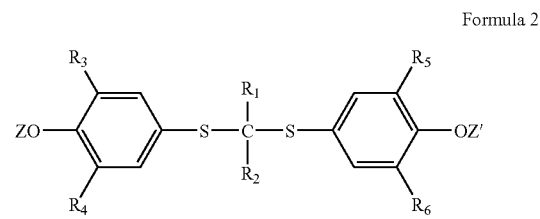

where Z and Z' are the same or different and are hydrogen, or the moiety —C(O)—$C_1$ to $C_6$ alkyl C(O)OA or the moiety —C(O)—$C_3$ to $C_6$-alkenyl C(O)OA where A is an alkali metal or ammonium cation and alkyl and alkenyl are as previously defined, with the proviso that Z and Z' can not both be hydrogen.

Preferably, Z and Z' are different and are hydrogen and —C(O)—$C_1$-$C_6$ alkyl C(O)OA most preferably hydrogen and the group —C(O)—$CH_2$—C(O)OA. The above substitution reaction is typically carried out from 30 minutes to about six hours in an organic solvent.

As noted, two probucol derivatives may be formed, i.e., the desired mono substitution product, where Z and Z' are different and are hydrogen and the moiety —C(O)—$C_1$ to $C_6$-alkyl C(O)OA or the moiety —C(O)—$C_3$ to $C_6$ alkenyl-C(O)OA where A is an alkali metal or ammonium cation and alkyl, and alkenyl are as previously defined or the disubstitution product, where Z and Z' are the same and are the moiety the moiety —C(O)—$C_1$ to $C_6$-alkyl C(O)OA or the moiety —C(O)—$C_3$ to $C_6$ alkenyl-C(O)OA where A is an alkali metal or ammonium cation and alkyl, and alkenyl are as previously defined.

The reaction mixture to produce the compounds of Formula 2 has a pH of from about 9 to about 14 and typically contains the unreacted probucol or probucol derivative as well as the mono and di substitution products of Formula 2. As such, and as a further embodiment of the present invention, an organic hydrocarbon solvent having the formula $C_nH_{2n+2}$ where n is an integer from 5 to 12 is added to this highly basic reaction mixture formed from the reaction of acid anhydride and probucol or probucol derivative. The hydrocarbon solvent dissolves unreacted probucol or probucol derivative and leaves a solution of the alkali metal or ammonium salts of the compounds of Formula 2 in the solvent R—C(O)R' where R and R' are as previously defined.

The reaction mixture of the compounds of Formula 2 is acidified in the presence of the same or a different organic hydrocarbon solvent that was previously used to remove the unreacted probucol or probucol derivative. In this way, the pH of such reaction mixture formed in reaction step (2) is reduced to less than 7 and then an organic hydrocarbon solvent having the formula $C_nH_{2n+}$ where n is an integer from 5 to 12 is added to the reduced pH reaction mixture. The hydrocarbon solvent preferentially dissolves the compounds of Formula 2 where Z and Z' are different and are hydrogen and the moiety —C(O)—$C_1$ to $C_6$ alkyl C(O)OH or the moiety C(O)—$C_1$ to $C_6$ alkenyl C(O)OH where alkyl and alkenyl are as previously defined.

It is preferred that the integer n of the hydrocarbon solvent is 6 to 9, Most preferably the hydrocarbon solvent is hexane, heptane or octane.

The formation of the acidified solution of the compounds of Formula 2 using the hydrocarbon solvent is carried out at temperatures >40° C. but not above 150° C. Preferably the temperature of the solvent-forming solution is about 45° to about 85° C.

As a final step in the process of the present invention used to prepare the water soluble probucol compounds is the purification of the compounds of Formula 2, i.e., the compounds where Z and Z' are the same or different and are hydrogen, or the moiety —C(O)—$C_1$ to $C_6$ alkyl C(O)OH or the moiety —C(O)—$C_3$ to $C_6$-alkenyl C(O)OH where alkyl and alkenyl are as previously defined, with the proviso that Z and Z' can not both be hydrogen.

As such, the compounds of Formula 2 obtained as a solution as set forth above are separated from the hydrocarbon solvent or the dibasic ester solvent as a solid material by conventional means (cooling, distillation to remove the solvent, etc.). This solid material is then redissolved in a typically aromatic solvent such as benzene, toluene, etc. and passed through a bed of impurity-removing compound, e.g., activated carbon, clay, silica gel, etc. The resulting solution is essentially a solution of the desired compound of Formula 2. Conventional separation processes produce the final crystalline product.

The present invention is described in detail in the examples set forth below which are provided by way of illustration only and therefore should not be considered as limiting the scope of the invention.

EXAMPLES

Synthesis of Water Soluble Derivatives of Probucol

General Process

Example 1

In an appropriately sized vessel, probucol (1 equivalent) and acetone (60 weight percent) are combined. With agitation potassium tert-butoxide (0.67 equivalent) is charged and the resultant solution warmed to ~40° C. for about 45 minutes. Succinic anhydride (0.67 equivalent) is charged and the system stirred at ~40° C. for at least 30 minutes. A dark reaction mixture forms which is a combination of the salts of di-succinylated probucol (DSP), mono-succinylated probucol (MSP) and unreacted probucol (PRO). The ratio of DSP:MSP:PRO is about 4:29:67.

Example 2

The reaction mixture of Example 1 is cooled to ~30° C., water is added and the pH of the reaction mixture is adjusted to >13 with 45% aqueous potassium hydroxide. The aqueous system is extracted three times with heptane. The probucol-rich heptane extractions are saved for recycle, while the aqueous acetone phase is saved for trituration.

Example 3

To the acetone solution of Example 2, is charged acetone (20 volume percent) and the pH of the system is adjusted to <3 with 85 weight percent (wt %) aqueous phosphoric acid. The acidified solution is mixed for at least 30 minutes and the resulting solids, which are predominately dibasic potassium acid phosphate, are filtered and discarded. The lower, aqueous phase of the resulting two phase filtrate is separated and discarded, reserving the acetone phase.

Acetone is removed from the reserved phase by distillation and heptane is added. The resultant slurry is triturated at 75-85° C. for about 30 minutes and filtered. The solid residue is reserved for later extraction. Upon cooling, the product-rich heptane filtrate provides a solid that is approximately 25 mol percent of material having the ratio 2:98, DSP:MSP Example 4

This MSP-enriched material from Example 3 is dissolved in toluene, then washed with 45% KOH. The toluene solution is dried with potassium carbonate and the solids removed by filtration. The toluene solution is then passed through clay absorb 24/48 to remove DSP.

Example 5

The toluene solution collected from Example 4 is washed once with 43% aqueous $H_3PO_4$ and once with water. The toluene solution is distilled to dryness and slurried with hot heptane. The heptane slurry is cooled and filtered. The solid residue is MSP. It is washed with heptane and dried at 70° C. under vacuum. A yield of approximately 15 to 25 mol percent MSP is obtained.

Specific Process

Example 6

In an appropriate-sized vessel, probucol (500 g, 0.97 mol) and acetone (300 g) are combined. With agitation potassium tert-butoxide (73 g, 0.65 mol) is charged and the resultant solution warmed to ~40° C. for at least 45 minutes. Succinic anhydride (65 g, 0.65 mol) is charged and the system stirred at ~40° C. for at least 30 minutes. A dark reaction mixture forms which is a combination of the salt of di-succinylated probucol (DSP), the salt of mono-succinylated probucol (MSP) and unreacted probucol (PRO). The ratio of DSP: MSP:PRO is about 4:29:67.

The reaction mixture is cooled to ~30° C., water (300 g) is added and the pH of the reaction mixture is adjusted to >13 with 45% aqueous potassium hydroxide (KOH) (about 40 g). The aqueous system is extracted three times with heptane (513 g for each extraction). The probucol-rich heptane extractions are saved for recycle, while the aqueous acetone phase is saved for trituration.

To the above-saved acetone solution, acetone is charged (158 g) and the pH of the system is adjusted to <3 with 85 wt % aqueous phosphoric acid (145 g). Additional acetone (200 g) is charged and the acidified solution is mixed for at least 30 minutes. The lower, aqueous phase is separated and discarded, reserving the acetone phase.

Acetone is removed from the reserved phase by distillation and heptane (665 g) is added. The resultant slurry is triturated at 80° C. for about 30 minutes and filtered. The solid residue is reserved for later extraction. The product-rich heptane filtrate is cooled to ~20° C., and the resulting precipitated MSP-enriched solids are collected by filtration. The 80° C. trituration process is repeated two more times with 410 g and 310 g of heptane, providing 133 g of a solid that is approximately 2:98, DSP:MSP. This MSP-enriched material is dissolved in toluene (500 mL), then washed with 45 g of 45% KOH. The toluene solution is mixed with potassium carbonate (44 g) for not more then 30 minutes and the solids removed by filtration. The toluene solution is then passed through clay absorb 24/48 (135 g, two passes). After each pass, the clay bed is washed twice with toluene (175 g).

The toluene solution collected from the passes through the clay absorb is washed once with 43% aqueous $H_3PO_4$ (300 g) and once with water (300 g). The toluene solution is distilled to dryness and the resulting residue slurried with heptane (275 g) at 80° C. for no longer than 30 minutes. The heptane slurry is cooled to 10° C. and filtered. The solid residue is MSP. It is washed with heptane (2×70 g) and dried at 70° C. under vacuum for approximately 3 hours. A yield of 97 g, 16 mol % is obtained.

We claim:

1. A process for the preparation of a water-soluble derivative of probucol having the following formula

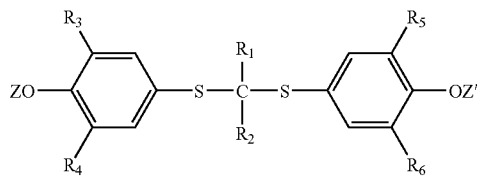

Formula 2 where $R_1$ and $R_2$ are the same or different and are —$C_1$-$C_6$ alkyl, —$C_3$-$C_6$ alkenyl or aryl, $R_3$, $R_4$, $R_5$ and $R_6$ are the same or different and are $C_1$-$C_6$ alkyl and Z and Z' are the same or different and are hydrogen or the group —C(O)—$C_1$ to $C_6$ alkyl-C(O)OH where Z and Z' can not both be hydrogen by (1) the reaction of a probucol compound of the formula

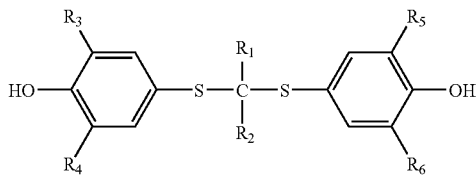

where $R_1$, $R_2$, $R_3$, $R_4$, $R_5$ and $R_6$ are as previously defined with a compound selected from the group consisting of alkali metal hydroxide, alkali metal alkoxide, alkyl ammonium alkoxide, alkyl ammonium hydroxide and mixtures thereof thereby forming an ammonium or alkali metal salt of said probucol compound (2) reacting said salt with a carboxylic acid anhydride to form a reaction mixture and (3) separating said water soluble probucol derivative from said reaction mixture the improvement comprising using as a solvent for reaction step 1 a compound having the formula R—C(O)—R', where R and R' are the same or different and are $C_1$-$C_6$ alkyl, $C_2$-$C_6$ alkenyl, $C_6$-$C_{12}$ aryl, $C_6$-$C_{12}$ aryl substituted with at least one $C_1$-$C_6$ alkyl, $C_5$-$C_{12}$ heteroaryl or $C_5$-$C_{12}$ heteroaryl substituted with at least one $C_1$-$C_6$ alky wherein the ratio of said solvent to the probucol derivative by weight is from about 2:1 to about 1:5, wherein the reaction temperature of step 1 is from about 15° to 75° C.

2. A process according to claim 1 where R and R' are the same or different and are $C_1$-$C_6$ alkyl.

3. A process according to claim 2 where R and R' are methyl or ethyl.

4. A process according to claim 3 where R and R' are methyl.

5. A process according to claim 1 wherein the ratio is from about 1:1 to about 3:10.

6. A process according to claim 5 wherein the ratio is 3:5.

7. A process according to claim 1 wherein said reaction temperature is from about 30° about 60° C.

8. A process according to claim 7 wherein said reaction temperature is from about 35° to about 45° C.

9. A process according to claim 1 wherein the pH of the reaction mixture formed in reaction step (2) is reduced to less than 7 and then an organic hydrocarbon solvent having the formula $C_nH_{2n+2}$ where n is an integer from 5 to 12 is admixed with the reduced pH reaction mixture at temperatures >40° C. but not above 150° C.

10. A process according to claim 9 wherein the integer n of the hydrocarbon solvent is 6 to 9.

11. A process according to claim 10 wherein the hydrocarbon solvent is hexane or heptane.

12. A process according to claim 1 wherein the temperature is about 45° C. to about 75° C.

* * * * *